US012630879B2

(12) United States Patent
Park et al.

(10) Patent No.: US 12,630,879 B2
(45) Date of Patent: May 19, 2026

(54) COMPOSITIONS FOR DIAGNOSIS, PREVENTION, OR TREATMENT OF FATTY LIVER DISEASE

(71) Applicants: HYSENSBIO, Gwacheon-si (KR); SEOUL NATIONAL UNIVERSITY R&DB FOUNDATION, Seoul (KR)

(72) Inventors: Joo Cheol Park, Seoul (KR); Dong Seol Lee, Seoul (KR); Geumbit Hwang, Ansan-si (KR)

(73) Assignees: HYSENSBIO, Gwacheon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 23 days.

(21) Appl. No.: 17/527,807

(22) Filed: Nov. 16, 2021

(65) Prior Publication Data

US 2022/0154278 A1      May 19, 2022

(30) Foreign Application Priority Data

Nov. 17, 2020     (KR) ......................... 10-2020-0153591

(51) Int. Cl.
*A61K 38/17* (2006.01)
*C12Q 1/6883* (2018.01)
(52) U.S. Cl.
CPC ........ *C12Q 1/6883* (2013.01); *A61K 38/1709* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 10,195,246 B2 * | 2/2019 | Park ..................... | C12N 5/0664 |
| 2016/0256409 A1 * | 9/2016 | Deshpande ............... | A61P 1/16 |
| 2017/0100458 A1 * | 4/2017 | Park ..................... | A61K 33/245 |
| 2019/0134017 A1 * | 5/2019 | Huff ..................... | C07D 307/22 |
| 2019/0153051 A1 | 5/2019 | Oh et al. | |
| 2019/0382446 A1 | 12/2019 | Park et al. | |

FOREIGN PATENT DOCUMENTS

| | | |
|---|---|---|
| WO | 2007/128884 A1 | 11/2007 |
| WO | 2017/190086 A1 | 11/2017 |
| WO | 2019143070 A1 | 7/2019 |

OTHER PUBLICATIONS

You-Mi Seo et al., "Copine-7 binds to the cell surface receptor, nucleolin, and regulates ciliogenesis and Dspp expression during odontoblast differentiation", Scientific Reports, Sep. 12, 2017, vol. 7, No. 11283, pp. 1-13 (13 pages).
Communication dated Oct. 22, 2024 in European Application No. 21 208 676.3.
Office Action issued Jun. 26, 2025 in Chinese Patent Application No. 202111361563.X.

* cited by examiner

*Primary Examiner* — Ronald T Niebauer

(74) *Attorney, Agent, or Firm* — Sughrue Mion, PLLC

(57) ABSTRACT

CPNE7 protein or a nucleotide encoding for CPNE7 protein, or compositions containing the CPNE7 or the nucleotide and their uses are disclosed. The protein, nucleotide, or composition is useful for preventing or treating fatty liver disease. The CPEN7 protein regulates the expression of the SREBF1 (SREBP1) gene or a gene encoding the same. The composition can be a pharmaceutical composition or a quasi-drug composition, a health functional food, or a dietary supplement, which is suitable for preventing or alleviating fatty liver disease.

9 Claims, 9 Drawing Sheets

(8 of 9 Drawing Sheet(s) Filed in Color)

Specification includes a Sequence Listing.

Heat map of the one-way Hierarchical Clustering
using Z-score for normalized value (log2 based)
(216 genes satisfying with fc2 & raw.p)

RNA-sequencing Results

| Gene | Description | KO/WT.fc | KO/WT.raw.pval |
|---|---|---|---|
| Srebf1 | sterol regulatory element binding transcription factor 1 | 2.004914 | 0.03083 |

*Cpne7*

*Srebf1*

```
                         SEQUENCE LISTING

<160> NUMBER OF SEQ ID NOS: 10

<210> SEQ ID NO 1
<211> LENGTH: 20
<212> TYPE: DNA
<213> ORGANISM: Unknown
<220> FEATURE:
<223> OTHER INFORMATION: mSREBF1

<400> SEQUENCE: 1
gcagtctgct ttggaacctc                                        20

<210> SEQ ID NO 2
<211> LENGTH: 20
<212> TYPE: DNA
<213> ORGANISM: Unknown
<220> FEATURE:
<223> OTHER INFORMATION: mSREBF1

<400> SEQUENCE: 2
cctcctgtgt acttgcccat                                        20

<210> SEQ ID NO 3
<211> LENGTH: 22
<212> TYPE: DNA
<213> ORGANISM: Unknown
<220> FEATURE:
<223> OTHER INFORMATION: hSREBF1

<400> SEQUENCE: 3
tgtccacaaa agcaaatctc tg                                     22

<210> SEQ ID NO 4
<211> LENGTH: 22
<212> TYPE: DNA
<213> ORGANISM: Unknown
<220> FEATURE:
<223> OTHER INFORMATION: hSREBF1

<400> SEQUENCE: 4
agtgtgtcct ccacctcagt ct                                     22

<210> SEQ ID NO 5
<211> LENGTH: 22
<212> TYPE: DNA
<213> ORGANISM: Unknown
<220> FEATURE:
<223> OTHER INFORMATION: hCPNE7

<400> SEQUENCE: 5
gtcttcacgg tggactacta ct                                     22

<210> SEQ ID NO 6
<211> LENGTH: 21
<212> TYPE: DNA
<213> ORGANISM: Unknown
<220> FEATURE:
<223> OTHER INFORMATION: hCPNE7
```

-continued

```
<400> SEQUENCE: 6
atgcgtgtcg tacacctcaa a                                                21

<210> SEQ ID NO 7
<211> LENGTH: 21
<212> TYPE: DNA
<213> ORGANISM: Unknown
<220> FEATURE:
<223> OTHER INFORMATION: mGapdh

<400> SEQUENCE: 7
aggtcggtgt gaacggattt g                                                21

<210> SEQ ID NO 8
<211> LENGTH: 23
<212> TYPE: DNA
<213> ORGANISM: Unknown
<220> FEATURE:
<223> OTHER INFORMATION: mGapdh

<400> SEQUENCE: 8
tgtagaccat gtagttgagg tca                                              23

<210> SEQ ID NO 9
<211> LENGTH: 21
<212> TYPE: DNA
<213> ORGANISM: Unknown
<220> FEATURE:
<223> OTHER INFORMATION: hGAPDH

<400> SEQUENCE: 9
agggctgctt ttaactctgg t                                                21

<210> SEQ ID NO 10
<211> LENGTH: 21
<212> TYPE: DNA
<213> ORGANISM: Unknown
<220> FEATURE:
<223> OTHER INFORMATION: hGAPDH

<400> SEQUENCE: 10
ccccacttga ttttggaggg a                                                21
```

COMPOSITIONS FOR DIAGNOSIS, PREVENTION, OR TREATMENT OF FATTY LIVER DISEASE

CROSS-REFERENCE TO RELATED APPLICATION

This U.S. non-provisional patent application claims priority under 35 U.S.C. § 119 to Korean Patent Application No. 10-2020-0153591, filed on Nov. 17, 2020, in the Korean Intellectual Property Office, the disclosure of which is hereby incorporated by reference in its entirety.

SEQUENCE LISTING

The content of the electronically submitted sequence listing, file name: Sequence_Listing_As_Filed.txt; size: 2,099 bytes; and date of creation: Nov. 16, 2021, filed herewith, is incorporated herein by reference in its entirety.

BACKGROUND

1. Field

The present disclosure relates to a composition for preventing or treating fatty liver disease, and more particularly, to the composition for preventing or treating a fatty liver disease associated with the accumulation of intracellular inflammatory cells or lipid droplets regulated by the concentration of CPNE7 protein or a gene thereof present in the body.

2. Description of the Related Art

Fatty liver is a disease resulting from excessive accumulation of fat in the liver and is defined as a case where the weight due to intrahepatic fat deposition is 5% or more of the weight in the liver.

Alcohol is a major cause of fatty liver. Thus, it is classified as fatty liver by drinking and fatty liver that is not, the former is called alcoholic fatty liver, and the latter is called non-alcoholic fatty liver disease (NAFLD).

Non-alcoholic fatty liver disease (NAFLD) refers to the case where the cause of fatty liver is not due to alcohol among them, and includes a series of processes ranging from simple steatosis in the liver to non-alcoholic SteatoHepatitis (NASH), cirrhosis, and is the most common disease among chronic liver diseases and is known to be closely related to type 2 diabetes, obesity, and metabolic syndrome.

Severe progression of the non-alcoholic fatty liver leads to non-alcoholic steatohepatitis (NASH). Fattyhepatitis is a dangerous stage compared to simple fatty liver, and in combination with hepatitis B or other health problems, it can develop liver cirrhosis or liver cancer.

Although no particular pathological symptoms appear in the simple steatosis stage, it can proceed to non-alcoholic steatohepatitis, liver fibrosis, and liver cirrhosis if not well managed, leading to serious complications, and also to hepatocellular carcinoma in very few patients.

Studies on chronic disease-causing transcripts have been studied for a long time by several researchers, and as a result, SREBP (Sterol regulatory element-binding protein) is well known to date as a transcription factor that is key in regulating the expression of fat metabolism-related enzymes. This SREBPs (Sterol regulatory-element binding proteins) gene, also named SREBF1, was first reported as a transcription factor that regulates the promoter of genes involved in cholesterol biosynthesis and the LDL receptor (LDLR) pathway.

SREBPs are well conserved from yeast to human and control the expression of genes that regulate intracellular lipid homeostasis. SREBP has three types of isoforms, 1a, 1c, and 2. It is known that SREBP-1a and SREBP-1c are mainly involved in the synthesis of fatty acids and triglycerides, and SREBP-2 is involved in cholesterol metabolism. In particular, SREBP1c regulates fatty acid and triglyceride biosynthesis in fatty biosynthetic organs such as the liver. SREBP-1 involved in the synthesis of fatty acids contains SRE-1 and an E-box motif, which are DNA binding sites that bind to transcription in the nucleus.

Although the causes and seriousness of fatty liver have been revealed, there are many cases in which fatty liver patients who should improve symptoms through dietary regulation and exercise do not tolerate them, and there is no established alleviating or treating agents for patients who are suspected of having or who have non-alcoholic fatty liver disease.

In particular, it is not desirable to present only weight loss as a measure for the non-alcoholic fatty liver disease since it is generally difficult for patients with a normal prescription for weight loss or obese patients to achieve a large improvement in lifestyle for significant weight loss.

Therefore, there is a need to develop a therapeutic drug for fatty liver for substantial treatment of fatty liver other than diet control and exercise, particularly for non-alcoholic fatty liver treatment.

Under these circumstances, as a result of intensive research efforts to develop a method capable of preventing or treating non-alcoholic fatty liver disease, the present inventors have confirmed that the use of the CPNE7 protein or a gene thereof can prevent or treat fatty liver disease through modulation of SREBP 1 activity involved in fatty acid synthesis in the liver, thereby completing the present invention.

The composition according to an embodiment of the present invention is intended for use in the prevention of fatty liver disease.

A composition according to another embodiment of the present invention is intended for use in the treatment of fatty liver disease.

The objects of the present invention are not limited to those mentioned above, and further objects which are not mentioned will be apparent to those skilled in the art from the following description.

SUMMARY OF THE INVENTION

According to an aspect of the present invention for solving the above technical problem, there is provided a pharmaceutical composition for preventing or treating a fatty liver disease comprising a CPNE7 protein or a gene thereof.

Here, the pharmaceutical composition can modulate the expression of SREBP1.

Here, the pharmaceutical composition is capable of modulating the accumulation of intracellular inflammatory cells or lipid droplets.

Here, the pharmaceutical composition can modulate SREBP1 gene (SREBF1) expression in hepatocytes.

Here, the hepatocytes may be HepG2 cells.

Here, the pharmaceutical composition can regulate the accumulation of hepatocytes with expanded cytoplasm, inflammatory cells, or lipid droplets in liver tissue.

Here, the pharmaceutical composition may further comprise a pharmaceutically acceptable carrier, an excipient, or a diluent.

Here, wherein the pharmaceutical composition modulates one or more processes selected from the group consisting of a small molecule metabolic process, a lipid metabolic process, a cellular lipid metabolic process, an organic acid metabolic process oxidation-reduction metabolic process, a carboxylic acid metabolic process, oxoacid metabolic process, a monocarboxylic acid metabolic process, a lipid biosynthetic process, a fatty acid metabolic process, a steroid metabolic process, a steroid biosynthetic process, a sterol metabolic process, a cholesterol metabolic process, a secondary alcohol metabolic process, a sterol biosynthetic process, a purine nucleoside bisphosphate metabolic process, a nucleoside bisphosphate metabolic process, a cholesterol biosynthetic process) and a secondary alcohol biosynthetic process.

Here, the fatty liver disease may be type 2 diabetes mellitus, obesity, and metabolic syndrome, intrahepatic fat deposition, non-alcoholic steatohepatitis, alcoholic steatohepatitis, liver fibrosis, cirrhosis, or liver cancer.

According to another aspect of the present invention, there is provided a method for preventing or treating fatty liver disease, comprising administering the pharmaceutical composition to a non-human individual.

According to another aspect of the present invention, there is a method for detecting a CPNE7 protein or a gene thereof using primers, probes, or antibodies capable of detecting the expression of the CPNE7 protein or a gene thereof provide information necessary for the diagnosis of fatty liver disease.

According to another aspect of the present invention, a quasi-drug composition can be provided for preventing or alleviating fatty liver disease, comprising the CPNE7 protein or a gene thereof.

According to another aspect of the present invention, a nutraceutical composition can be provided for preventing or alleviating fatty liver disease, comprising the CPNE7 protein or a gene thereof.

Advantageous Effects

According to embodiments of the present invention, the compositions may allow for the prevention of fatty liver disease by modulating the accumulation of intracellular inflammatory cells or lipid droplets or by modulating accumulation of hepatocytes with expanded cytoplasm, inflammatory cells, or lipid droplets in liver tissue.

According to another embodiment of the present invention, the composition may be used to treat fatty liver disease by inhibiting the accumulation of intracellular inflammatory cells or lipid droplets or by inhibiting accumulation of hepatocytes with expanded cytoplasm, inflammatory cells, or lipid droplets in liver tissue.

The effects of the present invention are not limited to those mentioned above, and other effects not mentioned may be clearly understood by those skilled in the art from the following description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows the population with similar levels of expression as a heat map. The upper graph of FIG. 3B shows the number of genes that were increased or decreased by at least 2-fold in the experimental group compared to the control group for RNA sequencing, and the lower graph shows a statistically significant number of ($p<0.05$) genes in the gene that was increased or reduced by 2-fold. FIG. 3C showed the top 20 terms in the field of biological processes when this gene was subjected to gene ontology enrichment analysis. The red and underlined portions corresponded to 10, which are 50% of the top 20 terms with fat-related processes.

FIG. 4A shows the results of the RNA sequencing that SREBP1, a transcription factor that plays an important role in the development of non-alcoholic fatty liver disease, was increased about 2-fold in the liver of the CPNE7 knockout mice. FIG. 4B shows results obtained by performing a technical repeat with a sample subjected to RNA sequencing and a biological repeat with another new sample in order to verify the results of RNA sequencing. Both results confirmed an increase in SREBP1 in the experimental group compared to the control group.

FIG. 5A shows the results of transfection of the CPNE7 gene into the HepG2 cell line, and it was confirmed that the expression of the CPNE7 gene was increased in the group transfected with the CPNET7 gene as compared with the control group. FIG. 5B is a graph showing a decrease in SREBP1 gene (SREBF1) expression in the group transfected with the CPNE7 gene compared to the control group.

FIG. 7A is a graph showing CPNE7 gene expression and FIG. 7B is a graph showing SREBP1 gene (SREBF1) expression.

DETAILED DESCRIPTION OF THE EMBODIMENTS

Figure 1:
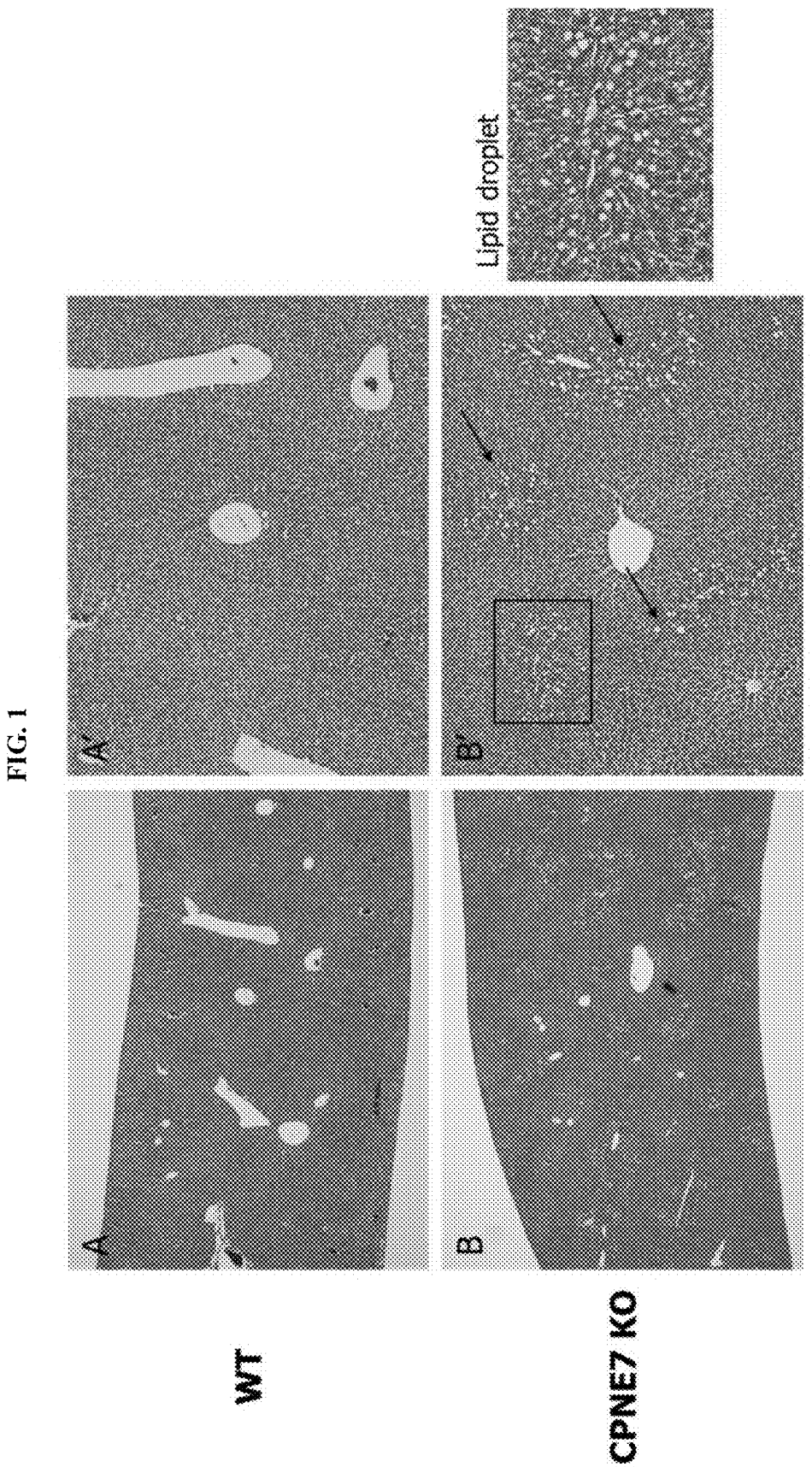
FIG. 1 is a result of analyzing the liver tissue of a control group (WT) and experimental group CPNE7 knockout (CPNE7 KO) mice through hematoxylin & eosin staining. Panel A shows a control, normal mice liver tissue staining, and panel A' is an enlarged photograph of panel A. No manifestations of any fatty liver disease such as lipid droplets were seen in the control group. Panel B shows the staining of liver tissue of CPNE7 knockout mice as an experimental group, and panel B' was observed to partially generate lipid droplets in an enlarged photograph of panel B as compared with the control group. The lipid droplets are indicated by arrows and the right picture of panel B' is the result of enlarging the box part of panel B', showing more pronounced lipid droplets.

Objects and advantages of the present invention, and technical configurations for achieving them, will become apparent with reference to the embodiments described in detail below in conjunction with the accompanying drawings. In the description of the present invention, when it is determined that a specific description of a known function or configuration may unnecessarily obscure the gist of the present invention, the detailed description thereof will be omitted. And the following terms are defined terms in consideration of the donation in the present invention, which may vary according to the user, the intent or practice of the operator, etc.

However, the present invention is not limited to the embodiments disclosed below but may be embodied in various different forms. The examples are merely provided to complete the disclosure of the present invention and to fully illuminate the scope of the invention to those skilled in the art, and the invention is only defined by the scope of the claims. The definition should therefore be made on the basis of the disclosure throughout this specification.

In the present invention, "fatty liver" is defined as a case where the weight due to intrahepatic fat deposition is 5% or more of the weight in the liver. "Non-alcoholic fatty liver disease" refers to the case where the cause of fatty liver is not due to alcohol and can be defined as a term that includes all the series of processes from simple steatosis in the liver to steatohepatitis, cirrhosis.

In the present invention, the "fatty liver disease" is not particularly limited as long as it exhibits a therapeutic effect by the CPNE7 protein of the invention or a gene thereof and can be, for example, type 2 diabetes, obesity, and metabolic syndrome, intrahepatic fat deposition, non-alcoholic steatohepatitis, alcoholic steatohepatitis, liver fibrosis, cirrhosis or liver cancer.

"CPNE7 protein" may be defined as one of the Copine family, a calcium-dependent membrane-binding protein, encoded by the CPNE7 gene. The protein contains two N-terminal C2 domains and one Von Willebrand Factor A domain. To achieve the objectives of the present invention, various derived and/or forms of the CPNE7 gene and or protein may be used as long as the effects of the invention are achieved. A "wild-type" sequence is intended to include, as well as fragments of genes in which a portion of the sequence has been artificially modified to favor characteristics such as expression in cells or stability of proteins, and genes in which a portion of the sequence found in nature has been modified or both.

In the present invention, modification of the gene sequence of the CPNE7 protein may or may not involve modification of corresponding amino acid, and in the case where modification of an amino acid is involved, the gene resulting from such modification is one encoding a protein consisting of the amino acid sequence in which one or more amino acids are substituted, deleted, added and/or inserted in the protein encoded thereby, and may include mutants, derivatives, alleles, variants, and homologs.

When a mutation in a gene sequence does not involve modification of an amino acid in a protein, for example, a degenerate mutation may exist, and such degenerate mutants may also be included in the gene of the present invention.

Modifications of artificial gene sequences can be made by methods well known to those skilled in the art, such as site-directed mutagenesis (Kramer et al., 1987), error-prone PCR (Cadwell, R. C. et al. and G. F. Joyce. 1992. PCR methods Appl., 2:28-33.), point mutagenesis (Sambrook and Russel, Molecular Cloning: A Laboratory Manual, 3rd Ed. 2001, Cold Spring Harbor Laboratory Press.), etc.

The proteins used in the examples of the present invention can be prepared using methods known in the art. In one embodiment, the method of producing a protein is using genetic recombination techniques.

For example, a vector comprising the corresponding gene encoding the protein can be transferred to a prokaryotic or eukaryotic cell such as an insect cell, a mammalian cell, expressed and then purified for use. The plasmid may be used by cloning the gene in question into an expression vector such as pET28b (Novagen) and transferring it into a cell line, followed by purification of the expressed protein, but is not limited thereto. The synthesized protein can be separated and purified by column chromatography, including precipitation, dialysis, ion-exchange chromatography, gel-permeation chromatography, HPLC, reverse-phase-HPLC, preparative SDS-PAGE, affinity column using anti-screening protein antibody, etc.

In one embodiment of the present invention, the CPNE7 gene and protein are from a mammal, such as an ape, a human, etc., and in particular from a human. The CPNE7 gene and protein may also be used as long as their full length or fragments thereof achieve the effects herein, and the full-length sequence may refer to, for example, but not limited to, NM170684 (nucleic acids), NP733785 (amino acids) for mice and NM014427 (nucleic acid), NP055242 (amino acid) for humans with GenBank accession numbers.

In an embodiment according to the present disclosure, the above-described gene may be provided in the form of an expression vector operably linked to a promoter so as to allow expression in a cell in which the composition of the present disclosure is used.

The term "expression vector" of the present invention means a recombinant vector capable of expressing a gene of interest in a host cell of interest, which gene construct comprises essential regulatory elements operably linked to express a gene insert. The expression vector comprises expression control elements, such as initiation codon, termination codon, promoter, operator, etc., which are generally considered to be part of a nucleotide sequence encoding a polypeptide and must be functional in an individual when the genetic construct is administered and in frame with the coding sequence. The promoter of the vector may be constitutive or inducible.

The term "operably linked" of the present invention refers to a state in which a nucleic acid expression regulatory sequence and a nucleotide sequence encoding a protein or RNA of interest are functionally linked to perform a general function. For example, a promoter and a nucleic acid sequence encoding a protein or RNA can be operably linked to affect the expression of the coding sequence. An operative linkage with an expression vector can be produced using genetic recombination techniques well known in the art, and site-specific DNA cleavage and linkage can be carried out using enzymes and the like generally known in this art.

The term "prevention" of the present invention means any action that inhibits or delays the occurrence of fatty liver disease by administration of a pharmaceutical composition for preventing or treating fatty liver disease, comprising the CPNE7 protein of the invention or a gene thereof.

The term "treatment" of the present invention refers to all actions that allow treatment of fatty liver disease to be carried out by administering a pharmaceutical composition comprising the CPNE7 protein or a gene thereof of the invention as an active component to a subject in need of such treatment, thereby inhibiting fatty accumulation of hepatocytes in the liver.

The pharmaceutical composition of the present invention can be prepared in the form of a pharmaceutical composition for the treatment of fatty liver disease and/or fatty liver, which further comprises a suitable carrier (natural or unnatural carrier), excipient or diluent, which is conventionally used for the preparation of pharmaceutical compositions for the CPNE7 protein or gene thereof. Specifically, the pharmaceutical composition can be formulated and used in the form of a sterile injectable solution, each of which can be administered to fatty liver disease and/or a site induced by fatty liver according to conventional methods. In the present invention, carriers, excipients, and diluents that may be included in the pharmaceutical composition include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, mineral oil, collagen, etc. In the case of formulation, it can be prepared using diluents or excipients such as fillers, extenders, binders, wetting agents, disintegrating agents, and surfactants usually used. In particular, sterile aqueous solutions, non-aqueous solutions, suspensions, emulsions, lyophilized preparations, suppositories, ointments (e.g., dimensional liner, etc.), etc. may be comprised. As the non-aqueous solvent and suspending agent, propylene glycol, polyethylene glycol, vegetable oils such as olive oil, injectable esters such as ethyl oleate, etc., can be used. As the suppository base, witepsol, Macrogol, tween 61, cacao butter, laurin butter, glycerogeratin, etc., can be used.

The content of the CPNE7 protein or gene thereof contained in the pharmaceutical composition of the present invention is not particularly limited but may be contained in an amount of 0.0001 to 50 wt %, more preferably 0.01 to 20 wt %, based on the total weight of the final composition.

The pharmaceutical composition of the present invention can be administered in a pharmaceutically effective amount, and the term "pharmaceutically effective amount" means an amount sufficient to treat or prevent disease at a reasonable benefit/risk ratio applicable to medical treatment or prevention, and an effective dose level can be determined according to the severity of the disease, the activity of the drug, the age, body weight, health, sex of the patient, the sensitivity to the patient's drugs, the time of administration, the route of administration and the duration of the treatment of the rate of excretion of the inventive composition employed, the factors including the drugs used in combination or coincidental with the inventive compositions employed, and other factors well known in the medical arts. The pharmaceutical compositions of the present invention may be administered alone or in combination with known pharmaceutical compositions for treating fatty liver disease and/or fatty liver. Considering all of the above factors, it is important to administer a minimum amount of the maximum effect without side effects.

The dosage of the pharmaceutical composition of the present invention can be determined by those skilled in the art in consideration of the purpose of use, the severity of the disease, the age, body weight, sex, history of the patient, or the kind of the substance used as an active component. For example, the pharmaceutical composition of the present invention can be administered at about 0.1 ng to about 100 mg/kg, preferably 1 ng to 10 mg/Kg, per adult, and the dosage frequency of the composition is not particularly limited but may be administered once a day or several divided doses. The above dosages do not limit the scope of the invention in any respect.

In another aspect, the present invention provides a method of treating fatty liver disease, comprising administering a pharmaceutically effective amount of the pharmaceutical composition to a subject suffering from fatty liver disease. In another aspect, there is provided a method of treating fatty liver disease, comprising administering a pharmaceutically effective amount of the pharmaceutical composition to a non-human subject having fatty liver.

The term "individual" of the present invention may include, without limitation, a human in need of treatment for fatty liver disease and/or fatty liver, or a mammal, including non-human rats, livestock, etc.

The route of administration of the pharmaceutical composition for treating fatty liver disease and/or fatty liver of the present invention may be administered via any general route as long as the desired tissue can be reached. The pharmaceutical composition of the present invention is not particularly limited but may be administered as desired via a route such as oral administration or oral injection.

In yet another aspect, the present invention provides a quasi-drug composition for preventing or improving fatty liver disease, comprising the above CPNE7 protein or a gene thereof, or a quasi-drug composition for preventing or improving the fatty liver, comprising the above CPNE 7 protein or a gene thereof.

As used herein, the term "improvement" refers to any act of reducing at least the extent of a parameter, e.g., a symptom associated with a condition being treated.

In the present invention, the improvement can be understood to mean all actions in which the symptom of fatty liver disease is ameliorated or beneficial by administering a pharmaceutical composition comprising the CPNE7 protein of the present disclosure or a gene thereof as an active component to an individual in need of treatment of fatty liver disease, thereby inhibiting fatty accumulation of hepatic cells in the liver, or all actions, in which a pharmacological composition comprising a CPNE 7 protein of this disclosure or the gene thereof, as an effective component, is administered to the individual in demand of treatment for fatty liver, thereby preventing fatty accumulation in hepatic cells of the live.

The term "quasi-drug" of the present invention refers to articles that are milder in action than pharmaceuticals, among articles used for the purpose of diagnosing, treating, alleviating, alleviating, treating, or preventing a disease in a human or animal, for example, according to the pharmacist method, the quasi-drug is a substance other than an article used for pharmaceutical and includes a fiber/rubber product used for treating or preventing diseases of humans/animals, a substance similar to a substance that has little or no direct action on the human body and is not a mechanism or the machine, and a bactericidal/pesticidal agent for preventing infectious diseases.

In the present invention, the type and formulation of the above CPNE7 protein or the pharmaceutical composition containing the gene thereof are not particularly limited.

In yet another aspect, the present invention provides a functional health food composition for preventing or improving fatty liver disease and/or fatty liver comprising the CPNE7 protein or a gene thereof.

The term "food" of the present invention includes dairy products including meat, sausage, bread, chocolate, candies, snacks, confectionery, pizza, ramie, other noodles, gums, ice cream, various soups, beverages, teas, drinks, alcohol drinks, vitamin complexes, health functional foods, and health foods, etc., and includes all foods in a conventional sense.

The above health functional food is the same term as the food for special health use (FoSHU) and means a food product having a high medical and medical effect processed so that bioregulatory functions are efficiently exhibited in addition to nutrient supply. The term "function(ality)" as used herein means to control nutrients for the structure and function of the human body or to obtain a useful effect for health uses such as physiological action. The food of the present invention can be produced by a method commonly used in the art, and in such production, raw materials and components commonly added in the industry can be added. The formulation of the food can also be prepared without limitation, provided that it is a formulation recognized as a food. The composition for food of the present invention can be prepared in various forms of dosage form, has the advantage of using food as a raw material unlike general drugs and having no side effects, etc. that can occur during long-term dosing of drugs, and is excellent in carrying property, and the food of this invention can also be taken as an adjuvant for enhancing the effect of preventing or improving fatty liver disease and/or fatty liver.

The term "health functional food" refers to a food product having active health maintenance and an enhancing effect as compared with the general formula product, and a health supplement food refers to a food product for a health supplement purpose. In some cases, the terms health functional food, health food, and health auxiliary food may be used interchangeably.

Specifically, the above health functional food means a food product prepared by adding the CPNE7 protein of the present invention or a gene thereof to a food material such as a beverage, a tea, a flavoring agent, a gum, and a confectionery, or by encapsulating, pulverizing, suspending or the like, which brings about a certain effect on health when ingested, but it has an advantage that it does not have any adverse effect that can occur when a food product is used as a raw material for a long-term administration of a drug, unlike general drugs.

Since the food composition of the present invention can be consumed on a daily basis, a high effect can be expected for the prevention or improvement of fatty liver disease and/or fatty liver, and thus it can be very usefully used.

The food composition may further comprise a physiologically acceptable carrier, and the kind of the carrier is not particularly limited, and any carrier commonly used in the art may be used.

In addition, the food composition may include additional components that are commonly used in food compositions to enhance odor, taste, vision, etc. For example, vitamin A, C, D, E, B1, B2, B6, B12, niacin, biotin, folate, pantothenic acid, etc., may be included. It may also include minerals such as zinc (Zn), iron (Fe), calcium (Ca), chromium (Cr), magnesium (Mg), manganese (Mn), and copper (Cu). It may also contain amino acids such as lysine, tryptophan, cysteine, valine, etc.

In addition, the food composition may contain food additives such as antiseptics (potassium sorbate, sodium benzoate, salicylic acid, sodium dehydrocholate, etc.), bactericides (bleaching powder, high bleaching powder, sodium hypochlorite, etc.), antioxidants (butyl hydroxyanisole (BHA), butylhydroxytoluene (BHT), etc.) coloring agents (tar coloring agent, etc,), color-forming agents (sodium nitrite, sodium subacetate, etc), bleaching agent (sodium sulfite), seasonings (sodium MSG glutamate, etc), sweeteners (dulcin, cyclamate, sodium saccharin, etc) perfumes (vanillin, lactones, etc); expanding agents (alum, potassium D-tartrate, etc); reinforcing agents, emulsifiers, thickeners (daments), coating agents, screening agents, foam inhibitors, solvents, and conditioners. The additives are selected according to the kind of food and can be used in an appropriate amount.

The CPNE7 protein of the present invention or a gene thereof can be added as it is or used in combination with other food or food components and can be suitably used according to a conventional method. The mixed amount of the active component can be suitably determined according to the purpose of its use (prevention, health, or therapeutic treatment). Generally, in the manufacture of a food or beverage, the food composition of the present invention may be added in an amount of 50 parts by weight or less, specifically 20 parts by weight or less, relative to the food or beverage. However, when ingested for a long period of time for the purpose of health and hygiene, the content may be within the above range, and since there is no problem in terms of safety, the active component may also be used in an amount above the above range.

One example of the food composition of the present invention may be used as a health beverage composition, in which case it may contain as additional components various flavoring agents, natural carbohydrates, etc., such as conventional beverages. The above-mentioned natural carbohydrates may be monosaccharides such as glucose, fructose; disaccharides such as maltose, sucrose; polysaccharides such as dextrin, cyclodextrin; sugar alcohols such as xylitol, sorbitol, erythritol, etc. As the sweetening agent, natural sweetening agents such as thaumatin, *stevia* extract; synthetic sweeteners such as saccharin, aspartame, etc., can be used. The proportion of natural carbohydrates can generally be about 0.01 to 0.04 g, specifically about 0.02 to 0.03 g, per 100 ml of the health drink composition of the present invention.

In addition to the above, the health drink composition may contain various nutrients, vitamins, electrolytes, flavoring agents, coloring agents, pectic acid, salts of pectin acid, alginic acid, salt of alginic acids, organic acids, protective colloid thickeners, pH regulators, stabilizers, antiseptics, glycerin, alcohols, carbonating agents, etc. They may also contain flesh for the production of natural fruit juices, fruit juice beverages, or vegetable beverages. These components may be used independently or in combination. The proportion of such additives is not critical but is generally selected in the range of 0.01 to 0.1 parts by weight per 100 parts by weight of the health and beverage composition of the invention.

The food composition of the present invention may comprise various weight percents as long as the effect of preventing or alleviating fatty liver disease and/or fatty liver is exhibited, but specifically, it may comprise 0.00001 to 100 weight percent or 0.01 to 80 weight percent of the CPNE7 protein or gene thereof, relative to the total weight of the food composition, but is not limited thereto.

In another aspect of the present invention, there is provided a method for preventing or treating fatty liver disease and/or a method of preventing or treatment of fatty liver, comprising administering to a subject a composition comprising the CPNE7 protein or a gene thereof.

In another aspect, the present invention provides a method for inhibiting accumulation of fat in hepatocytes in the liver and/or inhibiting expression of SREBP1, comprising administering to a subject a composition comprising the CPNE7 protein or a gene thereof.

In another aspect of the present invention, there are provided a CPNE7 protein or a gene thereof comprising an amino acid sequence of the following general formula (1) or a composition comprising the same for inhibiting accumulation of inflammatory cells or lipid droplets in hepatocytes, and prophylactic or therapeutic use for fatty liver disease or fatty liver.

According to one embodiment of the present invention, the effect of deletion of the CPNE7 gene on the accumulation of lipid droplets in liver tissue was verified. As a result, it was observed that in the liver tissue of the CPNE7 knockout (CPNE7 KO) mice, lipid droplets were generated, unlike the liver tissues of the control normal mice.

FIG. 1 is a result of analyzing the liver tissue of a control group (WT) and experimental group CPNE7 knockout (CPNE7 KO) mice through hematoxylin & eosin staining. Panel A shows a control, normal mice liver tissue staining, and panel A' is an enlarged photograph of panel A. No manifestations of any fatty liver disease such as lipid droplets were seen in the control group. Panel B of FIG. 1 shows the staining of liver tissue of CPNE7 knockout mice as an experimental group, and panel B' was observed to partially generate lipid droplets in an enlarged photograph of panel B as compared with the control group. The lipid droplets are indicated by arrows and the right picture of panel B' is the result of enlarging the box part of panel B', showing more pronounced lipid droplets.

To confirm the difference in hepatocytes due to the lack of the CPNE7 gene, liver tissues of the control group (wild type) and the experimental group CPNE7 knockout mice were analyzed using a transmission electron microscope. Hepatocytes of the control (wild type) had no void space in the cytoplasm, and no lipid droplets were observed (see FIG. 2, panels A and B). On the other hand, in the hepatocytes of the experimental group (mice knockout in the CPNE7 gene), the cytoplasm was swollen, and a large number of empty spaces were observed, and lipid droplets were observed (arrows) between the cytoplasms (see FIG. 2, panels C and D).

Figure 3A:
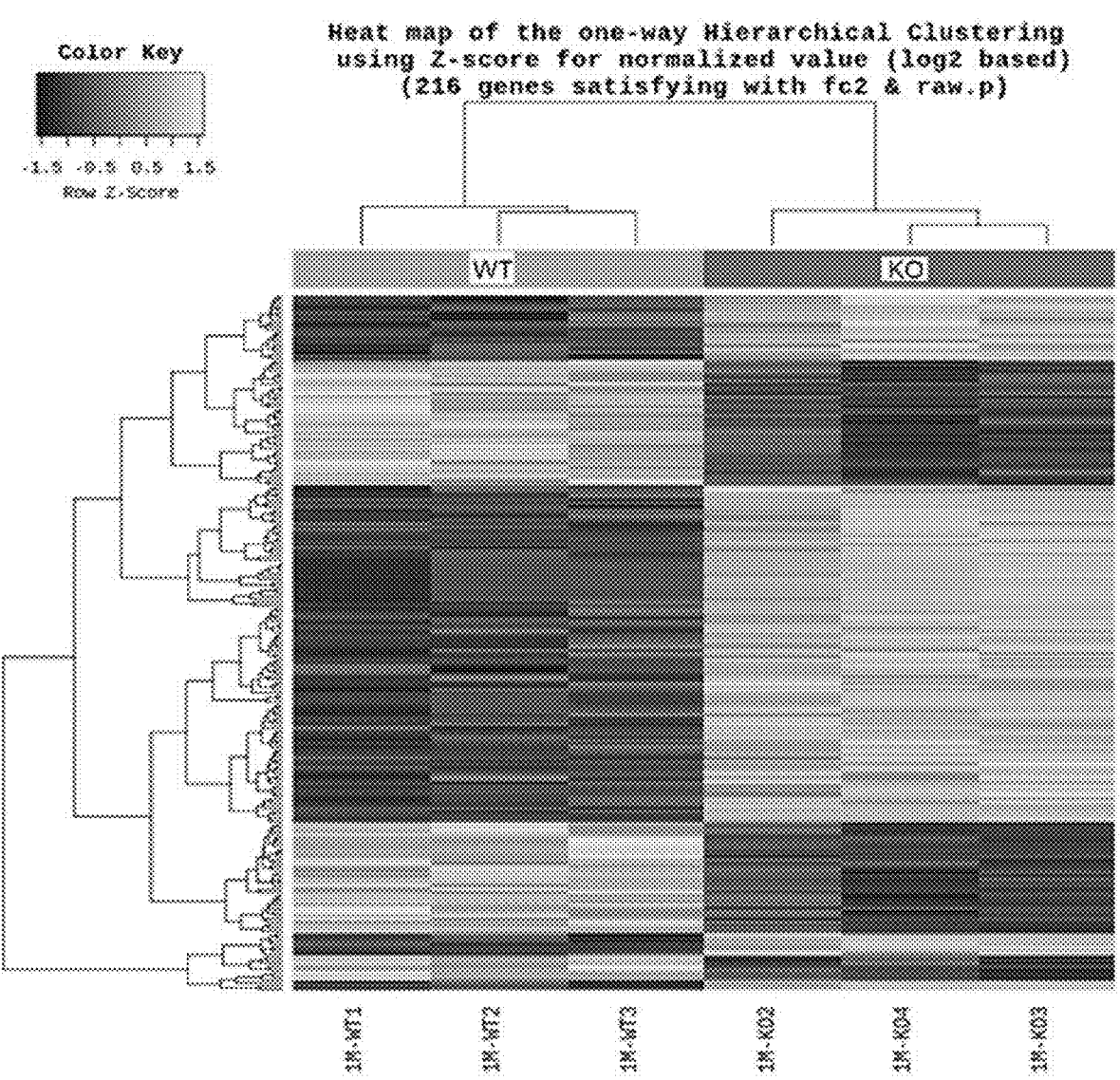
FIG. 3A to FIG. 3C show the results of analyzing the RNA sequences of various genes expressed in liver tissues of the control group and experimental group CPNE7 knockout mice.
Figure 3B:
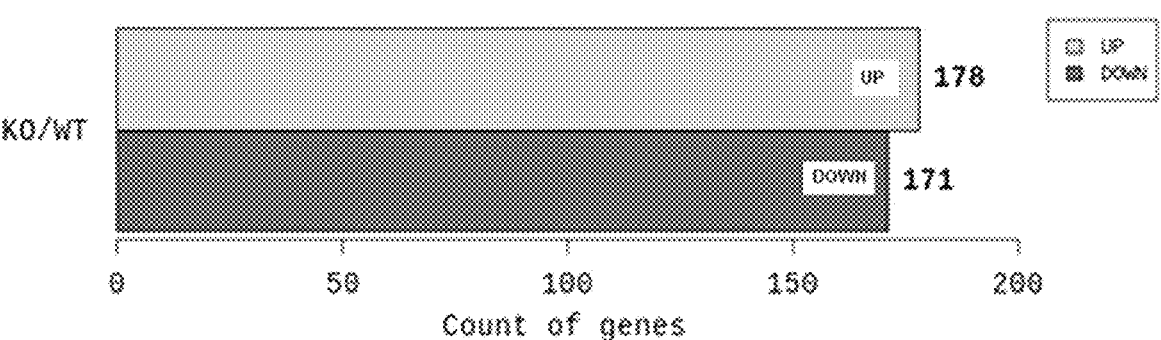
Figure 3B:
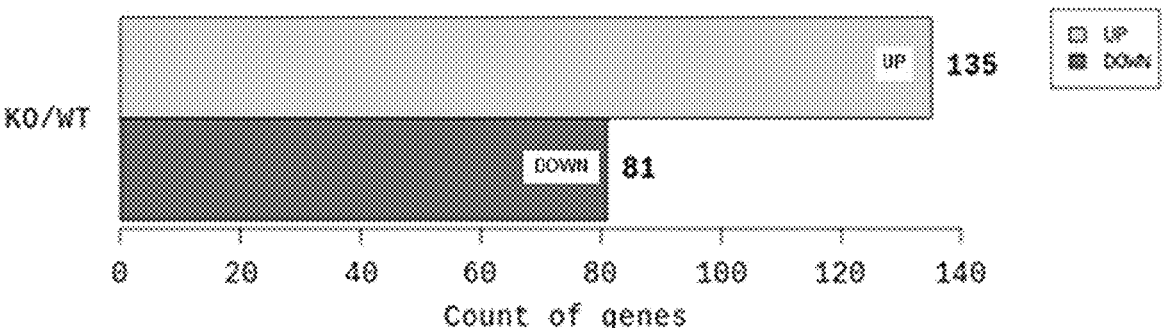
Figure 3C:

Here, The pharmaceutical composition according to an embodiment of the present invention may be involved in a small molecule metabolic process, a lipid metabolic process, a cellular lipid metabolic process, an organic acid metabolic process oxidation-reduction metabolic process, a carboxylic acid metabolic process, oxoacid metabolic process, a mono-carboxylic acid metabolic process, a lipid biosynthetic process, a fatty acid metabolic process, a steroid metabolic process, a steroid biosynthetic process, a sterol metabolic process, a cholesterol metabolic process, a secondary alcohol metabolic process, a sterol biosynthetic process, a purine nucleoside bisphosphate metabolic process, a nucleoside bisphosphate metabolic process, a cholesterol biosynthetic process) and a secondary alcohol biosynthetic process (See FIG. 3A-FIG. 3C).

FIG. 3A to FIG. 3C show the results of analyzing the RNA sequences of various genes expressed in liver tissues of the control group and experimental group CPNE7 knockout mice. FIG. 3A shows the population with similar levels of expression as a heat map. The upper graph of FIG. 3B shows the number of genes that were increased or decreased by at least 2-fold in the experimental group compared to the control group for RNA sequencing, and the lower graph shows a statistically significant number of ($p<0.05$) genes in the gene that was increased or reduced by 2-fold. FIG. 3C showed the top 20 terms in the field of biological processes when this gene was subjected to gene ontology enrichment analysis. The red and underlined portions corresponded to 10, which are 50% of the top 20 terms with fat-related processes.

Figures 4A, 4B:
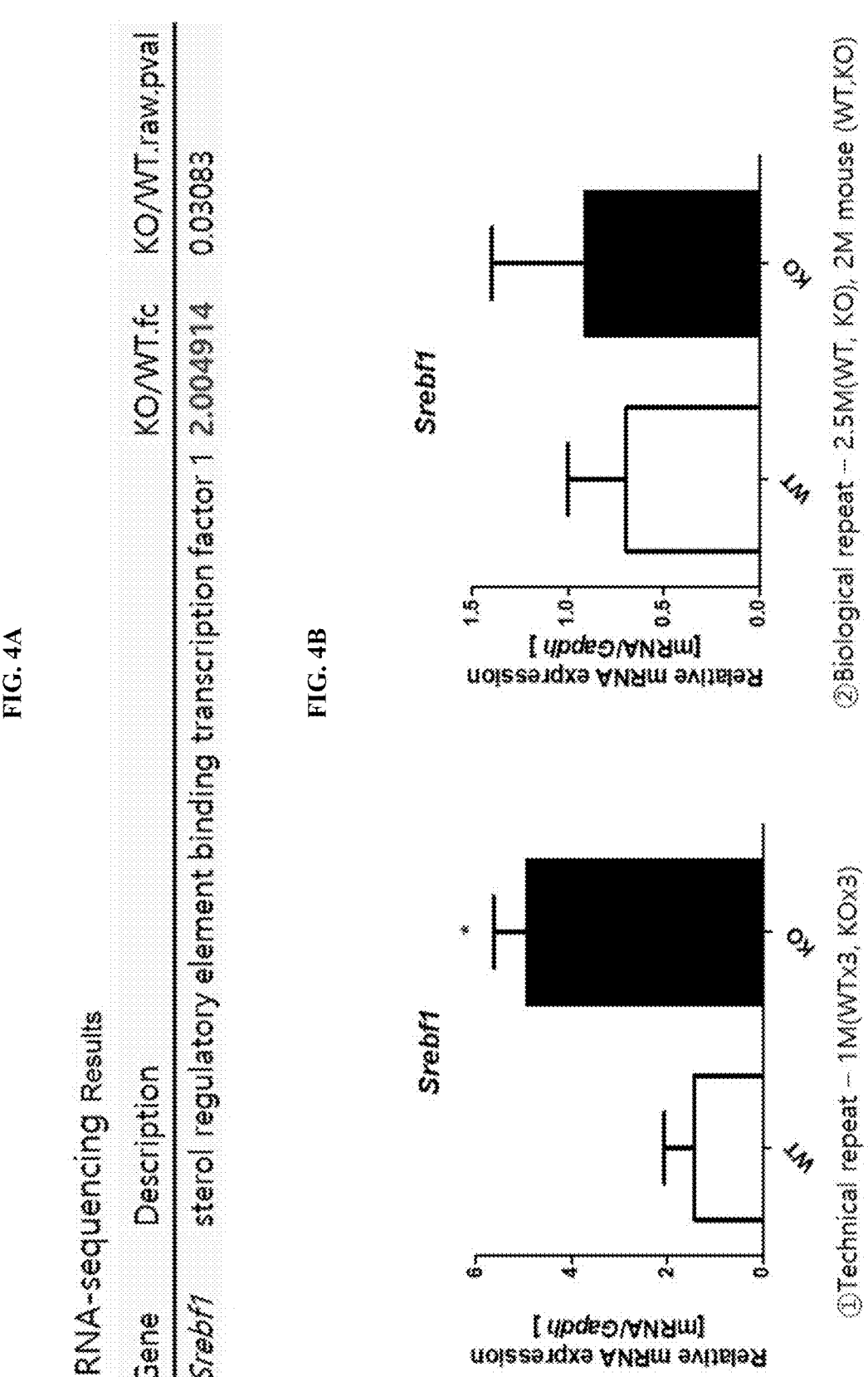
FIG. 4A and FIG. 4B show the results of comparing the expression of SREBP1 in the RNA nucleotide sequencing of various genes expressed in liver tissues of the control group (wild type) and experimental group CPNE7 knockout mice.

As a result of comparing the expression of SREBP1 by comparing the RNA nucleotide sequencing results of various genes expressed in liver tissues of the control group and the experimental group of the CPNE7 knockout mice, it was confirmed that the RNA sequencing result showed that the transcription factor that plays an important role in the development of non-alcoholic fatty liver disease was increased by about 2-fold in the livers of the CRE7 knockout mice. To verify the RNA sequencing result, the results of TR (Technical repeat) with the sample sent for RNA sequencing, and BR (Biological repeat) with a new sample are shown. Both results confirmed an increase in SREBP1 in the experimental group compared to the control group (FIG. 4B).

Figures 5A, 5B:
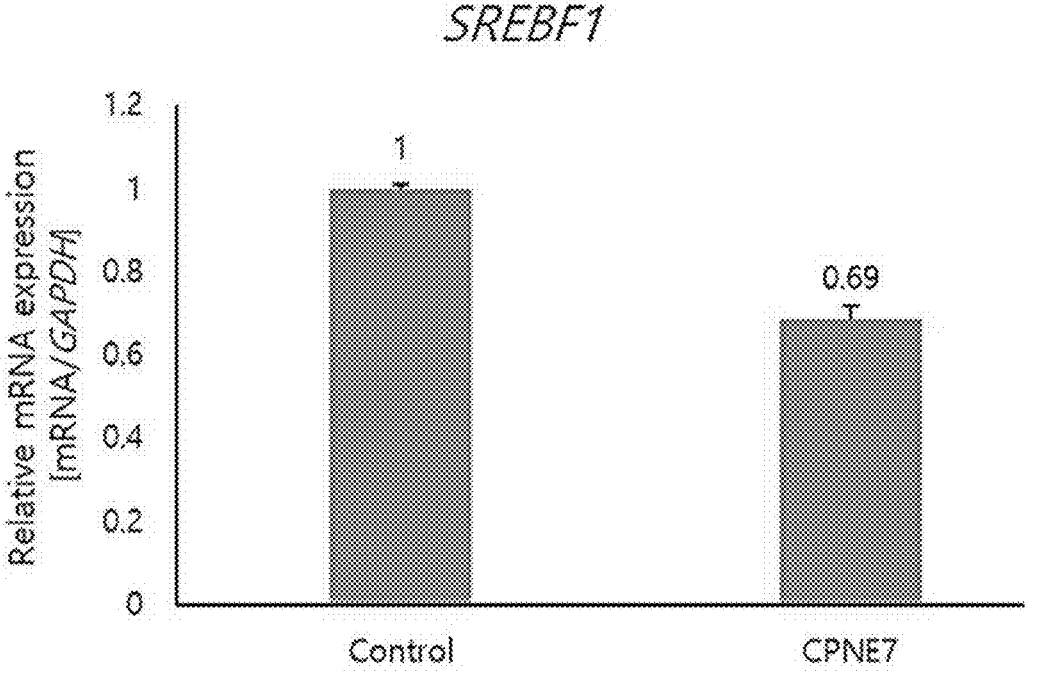
FIG. 5A and FIG. 5B show the results of the observation of the gene expression pattern of SREBP1 by transfection of the CPNE7 gene into HepG2 cells, which is a hepatocyte cell line, in order to confirm the correlation between the CPNET7 gene and the SREBP1 gene (SREBF1) in an in vitro experiment.

In order to confirm the correlation between CPNE7 and the SREBP1 gene (SREBF1) in an in vitro experiment, the CPNE7 gene was transfected into HepG2 cells of the hepatocyte cell line, and the SREBP1 gene expression pattern was observed. As a result, the CPNE7 gene was transfected into the HepG2 cell line. As a result, it was confirmed that the CPNE7 gene expression was increased in the group transfected with the CPNE7 gene compared to the control group (FIG. 5A). In addition, when the expression of the SREBP1 gene (SREBF1) was confirmed in the CPNE7 gene-transfected group, it was confirmed that the result was reduced compared to the control group (FIG. 5B).

Figure 6:
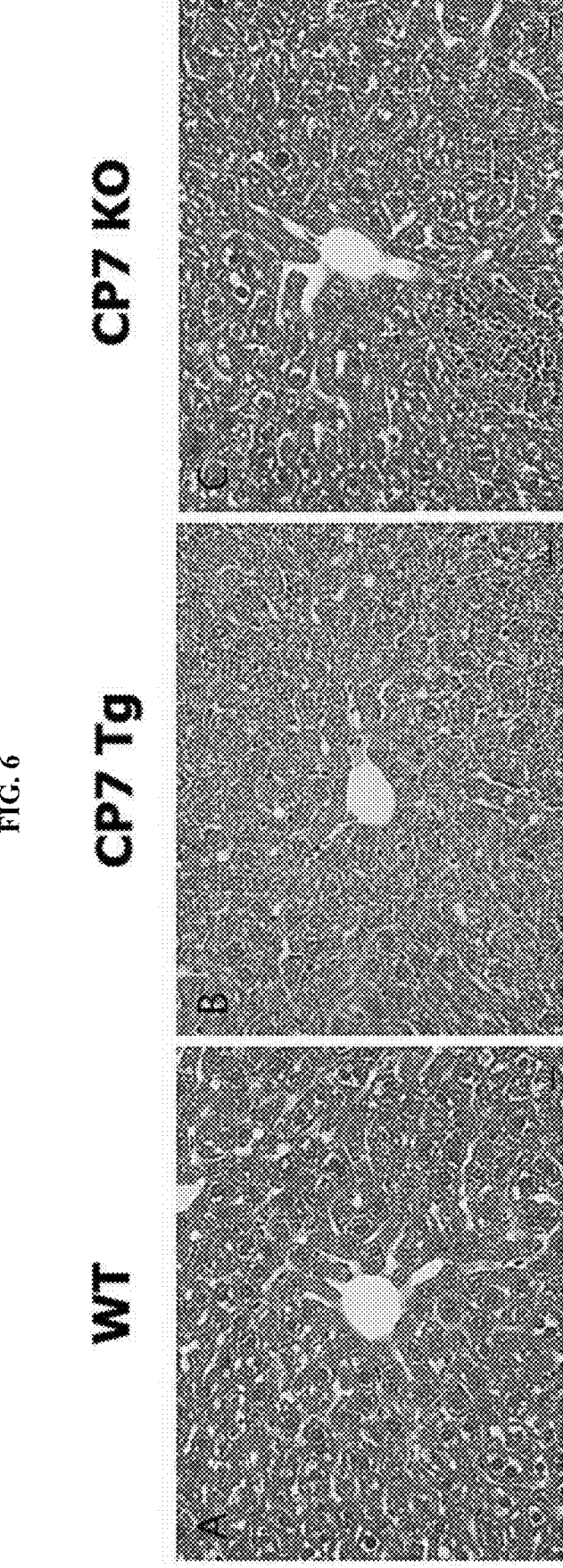
FIG. 6 shows the results of analyzing liver tissues of CPNE7 gene-overexpressed mice (CPNE7 Tg) of the control group and the experimental group or mice knockout in the CPNET7 gene by hematoxylin & eosin staining. Panel A shows the result of staining liver tissue of a control normal mice. Panel B shows that the liver tissue of the experiment group CPNE7 gene-overexpressed mice was stained, and no pathological aspects were confirmed. Panel C shows the staining of liver tissue of the CPNE7 knockout mice in the experimental group, and in contrast to the liver tissue in the control group or in mice overexpressing CPNE7, partially hepatocytes with expanded cytoplasm(hepatocellular ballooning) and large amounts of inflammatory cells were observed.

It is the result of analyzing the liver tissues of the control group (wild type) and the experimental group, mice over-expressing the CPNE7 gene (CPNE7 Tg) or mice lacking the CPNE7 gene by hematoxylin & eosin staining (FIG. 6). Specifically, Panel A is a result of staining liver tissue of a normal mice as a control group. Panel B shows that the liver tissue of the experiment group CPNE7 gene-overexpressed mice was stained, and no pathological aspects were confirmed. Panel C shows the staining of liver tissue of the CPNE7 knockout mice in the experimental group, and in contrast to the liver tissue in the control group or in mice overexpressing CPNE7, partially hepatocytes with expanded cytoplasm (hepatocellular ballooning) and large amounts of inflammatory cells were observed.

Figure 7A:
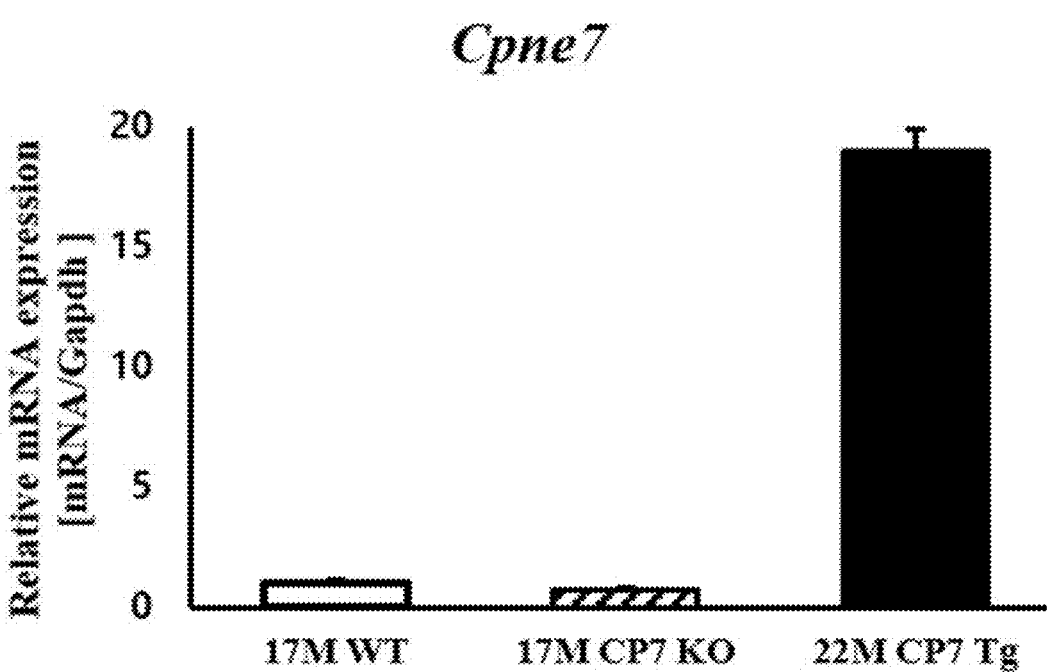
FIG. 7A and FIG. 7B are results of analyzing the correlation between CPNE7 and SREBP1 in the liver tissue of the control group and the experimental group mice in an in vivo experiment. RNA was extracted from liver tissue of control and CPNE7 gene-overexpressed mice or CPENE7 knockout mice, and expression of the CPNE7 and SRE BP1 gene (SREBF1) was measured.
Figure 7B:
Figure 7B:
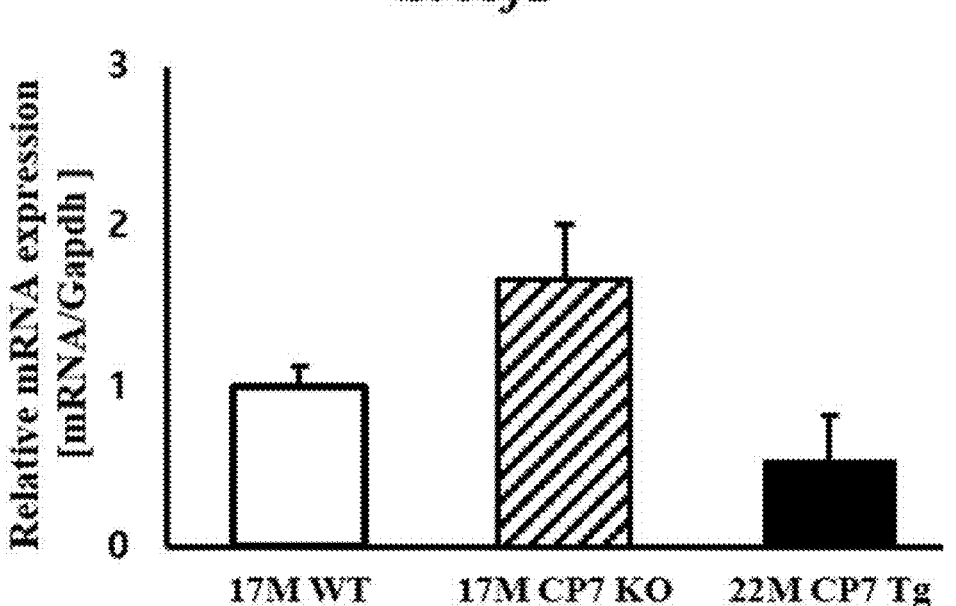

FIG. 7A and FIG. 7B are results of analyzing the correlation between CPNE7 and

SREBP1 in the liver tissue of the control group and the experimental group mice in an in vivo experiment. RNA was extracted from liver tissue of control and CPNE7 gene-overexpressed mice or CPENE7 knockout mice, and expression of the CPNE7 and SRE BP1 gene (SREBF1) was measured. FIG. 7A is a graph showing CPNE7 gene expression and FIG. 7B is a graph showing SREBP1 gene (SREBF1) expression. As can be seen from FIG. 7A and FIG. 7B, it was observed that, in the case of the CPNE7 gene overexpression mice, the SREBP1 gene (SREBF1) was expressed relatively less than the liver tissue of the control or CPNE7 knockout mice.

Hereinafter, exemplary embodiments of the present invention will be described in detail.

Example 1: Experimental Materials and Methods

Example 1-1. Preparation of Experimental Animals

Male C57BL/6J mice used as controls in this experiment were purchased from the company (Dooyeol Biotech, Seoul, Korea), and CPNE7 knockout mice (CPNE7 KO) were used as experimental groups were generated in a standard gene targeting manner. Vectors containing the EGFP coding region (EGFR) and the neomycin resistance cassette (NeoR) were cloned, which is related to the CPNE7 gene exon 5-7 base sequence.

The vectors were transformed into CMTI-1 ES cell lines from 129/SVEV mice using electroporation methods. After electroporation, G418/ganciclovir resistant colonies were selected and transplanted into surrogate mothers to generate progeny.

The CPNE7-overexpressed mice were prepared using a method such as the procedure of preparing a vector using the epithelial cell marker gene Keratin-14 (K14) promoter to specifically overexpress epithelial cells and then preparing CPNE7 knockout mice.

All mice used in the experiments were housed under about 20-25° C., about 45-55% humidity control in cages of a 12:12-hour light/dark cycle.

Normal mice and mice knockout in the CPNE7 knockout or overexpressed mice were subjected to histological analysis or genetic analysis after perfusion 1 month, 3 months, or 6 months of breeding. All experiments were used after approval by the Animal Care and Use Committee at Seoul National University (Seoul) facility.

Example 1-2. Hematoxylin & Eosin Staining

Mice domesticated for 3 months were sacrificed to excise liver tissue and fixed in 4% paraformaldehyde solution for 24 hours. After dehydration, it was embedded in paraffin, and the tissue was thin sectioned to a thickness of 5 μm. The paraffin of the tissue sections was removed with xylene and stained with hematoxylin and eosin after hydration. Samples were prepared after the dewatering and transparency processes.

Examples 1-3. Transmission Electron Microscopy Analysis 6-month-old mice are sacrificed to excise liver tissue and made approximately 1×1 mm in size, prefixed for 24 hours in 4% paraformaldehyde solution, and postfixed with 1% osmium tetroxide. The dehydration process was followed by embedding with a Spurr's resin and exfoliation followed by observation with a transmission electron microscope.

Examples 1-4. RNA Extraction and RNA Sequencing

RNA was extracted from liver tissue excised at the expense of 1-month-old mice using reagents (TRI Reagent®, TR 118, MRC, USA). The extracted RNA was quantified to be about 1 μg, and RNA sequencing was requested from Macrogen.

Examples 1-5. Cell Line Culture and Transfection

HepG2 cell line (KCLB 88065) was purchased from the Korea cell line and used. The HepG2 cell line was cultured in MEM medium supplemented with 10% heat-inactivated bovine serum at 37° C. containing 5% CO2. Transfection was performed using an expression vector encoding full-length human CPNE7 (purchased Origene (USA)), green fluorescent protein (GFP)-CPNE7 (NM_153636), and DDK (flag)-tagged CPNE7 (NM_153636).

Example 1-6. Real-Time Gene Amplification Analysis

Total RNA was extracted from liver tissue and HepG2 cell line (KCLB 88065, Korea Cell Line Bank) using reagent (TRI Reagent®, TR 118, MRC, USA). cDNA was then synthesized from the RNA using a Maxime Rt premix kit (25081, iNtRON). Real-time PCR was performed according to the manual on an ABI PRISM 7500 Sequence Detection System (Applied Biosystems, USA) using SYBR Green PCR Master Mix (Takara Bio, Japan).

After about 10 minutes at 95° C., PCR was performed under the conditions of 40 cycles at 95° C. for 15 seconds and at 60° C. for 1 minute, respectively. All reactions proceeded in triplicate, and PCR product levels were normalized based on the housekeeping gene GAPDH. Relative changes in gene expression were calculated using the comparative threshold cycle (CT) method. The primers used are as follows.

TABLE 1

| Gene | Forward | Reverse |
|------|---------|---------|
| mSREBF1 | GCAGTCTGCT TTGGAACCTC (SEQ ID NO: 1) | CCTCCTGTGT ACTTGCCCAT (SEQ ID NO: 2) |
| hSREBF1 | TGTCCACAAA AGCAAATCTC TG (SEQ ID NO: 3) | AGTGTGTCCT CCACCTCAGT CT (SEQ ID NO: 4) |
| HC-PNE7 | GTCTTCACGG TGGACTACTA CT (SEQ ID NO: 5) | ATGCGTGTCG TACACCTCAA A (SEQ ID NO: 6) |
| mGapdh | AGGTCGGTGT GAACGGATTT G (SEQ ID NO: 7) | TGTAGACCAT GTAGTTGAGG TCA (SEQ ID NO: 8) |

TABLE 1-continued

| Gene | Forward | Reverse |
|---|---|---|
| hGAPDH | AGGGCTGCTT TTAACTCTGG T (SEQ ID NO: 9) | CCCCACTTGA TTTTGGAGGG A (SEQ ID NO: 10) |

Example 2: Experimental Results

Example 2-1. Analysis of the Effect of CPNE7 Gene-Deficiency on the Accumulation of Lipid Droplets in Liver Tissue To compare the accumulation of lipid droplets in liver tissues of normal mice and CPNE7 knockout mice (CPNE7 KO), liver tissue of 3-month-old mice was observed using hematoxylin & eosin staining (FIG. 1).

Compared with the control group (FIG. 1, panels A and A'), an aspect was observed in which the accumulation of lipid droplets in liver tissue was increased in CPNE7 knock-out mice (FIG. 1, panels B and B').

Figure 2:
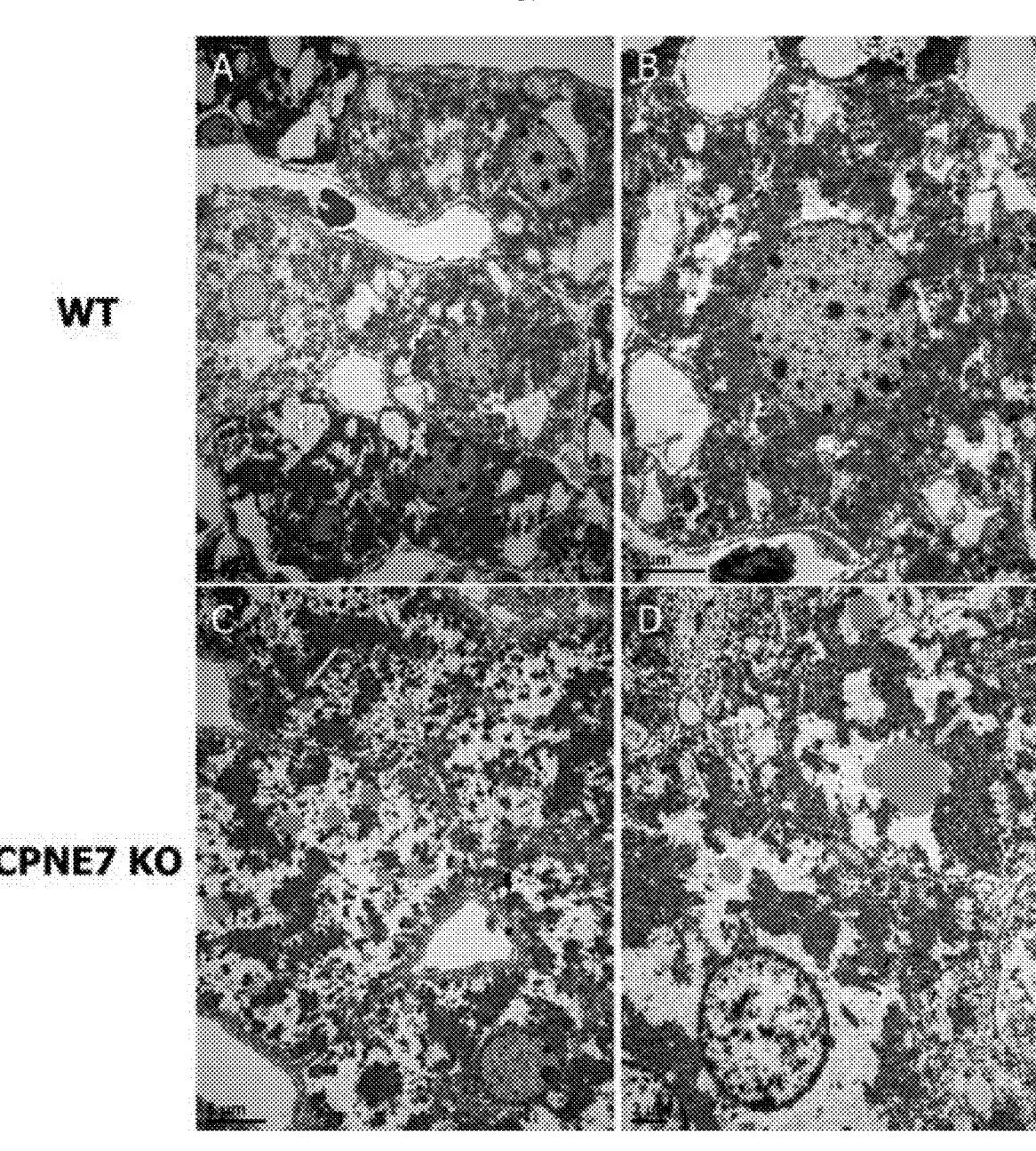
FIG. 2 shows the results of analyzing liver tissues of the control group and experimental group CPNE7 knockout mice using a transmission electron microscope. In panels A and B, the hepatocytes of the control group were observed, with no empty space in the cytoplasm, and no lipid droplets were observed. In panels C and D, when the hepatocytes of the experimental group (CPNE7 knockout mice) were observed, the cytoplasm was swollen, and a large number of empty spaces were observed, and lipid droplets were observed between the cytoplasms. Arrows indicate lipid droplets.

FIG. 2 shows the morphological characteristics of liver tissues of normal (panels A and B) and CPNE7 knockout mice (panels C and D) and the results of analysis of accumulation of lipoid using transmission electron micros-copy. Liver tissues of 6-month-old mice were removed to prepare samples for transmission electron microscopy analysis. As a result of the transmission electron microscopy analysis, in comparison with normal mice, hepatocytes of the CPNE7 knockout mice were observed to have a large number of empty spaces in the cytoplasm as the cytoplasm was expanded (hepatocellular ballooning).

Example 2-2. Comparison of Gene Expression Associated with Adipogenesis in Liver Tissues of Normal Mice and CPNE7 Gene Deficiency (CPNE7 KO) Mice In order to analyze the causes of swelling of hepatocytes and accumulation of lipid droplets in the histological analy-sis of FIGS. 1 and 2, RNA was extracted from liver tissues of mice knockout in the CPNE7 gene and normal mice that had been given a month, and RNA sequencing was per-formed (see FIGS. 3A-3C). As a result of the nucleotide sequencing, when the number of genes that differed by two or more times from each other using WT as a control group and CPNE7 KO as an experimental group in the graph was analyzed, there were 178 genes that increased and 171 genes that decreased in liver tissue of CPNE7knockout (CPNE7KO) mice (FIG. 3B). Of these, the number of statistically significant genes was found to be 135 for increased genes and 81 for decreased genes. Gene ontology enrichment analyses were performed on genes that were significantly different in expression between the control and experimental groups as described above, and most were observed with fat-related processes (FIG. 3C) by looking at the top 20 terms in bioprocessing analyses. Thus, the results in FIGS. 1, 2, and 3A-3C confirm that CPNE7 is associated with fatty liver disease.

Example 2-3. Effect of the CPNE7 Gene on the Expression of Factor SREBP1 Induced by Non-alcoholic Fatty Liver Generation It was confirmed that the SREBF1 (Sterol regulatory element binding transcription factor 1) gene, which is known as a transcription factor important for non-alcoholic fatty liver development, was comprised among the fat-related genes significantly different between the control group and the experimental group. SREBP1(Sterol regula-tory element binding protein1), a protein encoded by SREBF1, is a lipid homeostasis modulator that serves to increase the transcriptional activity of fat synthesis-related genes. In previous studies, it is known that excessive expres-sion of SREBP1 in the liver in mice leads to fatty liver, and conversely, deletion of SREBP1 in the induced fatty liver mice model improves fatty liver. As a result of the RNA sequencing in FIGS. 4A and 4B, it was confirmed that SREBF1 (SREBP1) was increased in the CPNE7 KO liver tissue compared to the control group, and this result was verified by repeated experiments.

Example 2-4. Analysis of Effects of Overexpression of CPNE7 on SREBP1

Expression in Liver Cell Line HepG2

In order to confirm the effect of overexpression of CPNE7 on SREBF1 (SREBP1) gene expression in the hepatocyte cell line, the expression of the SREBF1(SREBP1) gene was confirmed after overexpression of the CPEN7 gene using the liver cell line HepG2. A marked reduction in SREBF1 (SREBP1) gene expression was observed in one group overexpressing the CPNE7 gene compared to the control (FIGS. 5A and 5B). This result shows the potential of CPNE7 as a therapeutic agent for preventing or treating non-alcoholic fatty liver through regulation of SREBF1 (SREBP1) gene expression.

Example 2-5. Histological Analysis of Liver Tissues in CPNE7-Overexpressed Mice (CPNE7 Tg)

In FIG. 6, liver tissues of CPNE7-overexpressed (CPNE7 Tg) mice, normal mice, or CPNE7knockout (CPEN7 KO) mice were analyzed using hematoxylin & eosin staining. In liver tissues of CPNE7knockout (CPNE7 KO) mice com-pared to normal mice, cytoplasmic expanded hepatocytes (hepatocellular ballooning) and large amounts of inflamma-tory cells could be identified. However, no fatty liver lesions such as lipid droplets and hepatocytes with expanded cyto-plasm were observed in liver tissues of CPNE7-overex-pressed (CPNE7 Tg) mice.

Example 2-6. Gene Expression Analysis of Srebp1 in Liver Tissue of CPNE7-Overexpressed (CPNE7 Tg) Mice RNA was extracted from liver tissues of normal mice (WT), CPNE7 knockout (CP7 KO) mice, and CPNE7-overexpressed (CP7 Tg) mice to confirm the expression of CPNE7 and SREBF1 (SREBP1) genes. CPNE7 gene expression was reduced in liver tissue of CPNE7 knockout (CPNE7 KO) mice compared to that of normal mice and increased in liver tissues of CPNET7-overexpressed (CP-NET7 Tg) mice (FIG. 7A). SREBF1 (SREBP1) gene expression was increased in liver tissue of CPNE7 knockout (CPNE7 KO) mice, but it was confirmed that the expression was decreased in liver tissues of CPNET7-overexpressed (CPNET7 Tg) mice (FIG. 7B). Taken together with the above results, CPNE7 can prevent or treat non-alcoholic fatty liver disease through the regulation of SREBF1 (SREBP1) gene expression.

In the present specification and drawings, preferred embodiments of the present invention have been disclosed, and although specific terms are used, these are only used in a general sense to easily explain the technical content of the present invention and help the understanding of the present invention. It is not intended to limit the scope. It will be apparent to those skilled in the art that other modifications based on the technical concept of the present invention can be carried out in addition to the embodiments disclosed herein.

What is claimed is:

1. A method of treating non-alcoholic fatty liver disease of a subject in need thereof, comprising:
   administering to the subject an effective amount of a composition consisting of (a) an active component and (b) a pharmaceutically acceptable carrier, an excipient, or a diluent, wherein the active component consists of an unmodified full length CPNE7 protein or a fragment thereof or a gene encoding the unmodified CPNE7 protein or a fragment thereof, wherein said gene is contained in an expression vector and is operably linked,
   wherein the unmodified full length CPNE7 protein or a fragment thereof comprises two N-terminal C2 domains and one Von Willebrand Factor A domain, and
   wherein the subject has a non-alcoholic fatty liver in which intrahepatic fat deposition is 5% or more of a weight of liver of the subject.

2. The method of claim 1, wherein the administration of the composition modulates the expression of Sterol regulatory-element binding protein 1 (SREBF1).

3. The method of claim 1, wherein the administration of the composition modulates intracellular inflammatory cell or lipid droplets accumulation.

4. The method of claim 1, wherein the administration of the composition modulates Sterol regulatory-element binding protein 1 (SREBF1) gene expression in hepatocytes.

5. The method of claim 4, wherein the hepatocytes are HepG2 cells.

6. The method of claim 1, wherein the administration of the composition modulates accumulation of hepatocytes with expanded cytoplasm, inflammatory cells, or lipid droplets accumulation in liver tissue.

7. The method of claim 1, wherein the subject having the non-alcoholic fatty liver disease has type 2 diabetes, obesity, metabolic syndrome, non-alcoholic steatohepatitis, liver fibrosis, cirrhosis, or liver cancer.

8. The method of claim 1, wherein the active component consists of a wild type unmodified full length CPNE7 protein or a gene encoding the wild type unmodified full length CPNE7 protein.

9. The method of claim 1, wherein the active component consists of an unmodified full length CPNE7 protein having a GenBank accession number NP733785 or NP055242, or a gene encoding a wild type unmodified full length CPNE7 protein, said gene having a GenBank accession number NM170684 or NM014427.

* * * * *